(12) United States Patent
Bleuet et al.

(10) Patent No.: US 9,754,696 B2
(45) Date of Patent: Sep. 5, 2017

(54) RESOLUTION TEST CHART FOR X-RAY IMAGING SYSTEM AND METHOD OF FABRICATION

(71) Applicant: COMMISSARIAT A L'ENERGIE ATOMIQUE ET AUX ENERGIES ALTERNATIVES, Paris (FR)

(72) Inventors: Pierre Bleuet, Seyssins (FR); Christophe Constancias, Sarcenas (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 268 days.

(21) Appl. No.: 14/567,722

(22) Filed: Dec. 11, 2014

(65) Prior Publication Data
US 2015/0170779 A1 Jun. 18, 2015

(30) Foreign Application Priority Data
Dec. 13, 2013 (FR) ...................................... 13 62587

(51) Int. Cl.
G21K 1/10 (2006.01)
G01N 23/04 (2006.01)

(52) U.S. Cl.
CPC ............. *G21K 1/10* (2013.01); *G01N 23/04* (2013.01); *G21K 2207/00* (2013.01)

(58) Field of Classification Search
CPC ....... A61B 6/484; A61B 6/4291; A61B 6/583; A61B 6/4233; G01N 23/04; G01N 2223/303
See application file for complete search history.

(56) References Cited

U.S. PATENT DOCUMENTS

| 5,812,629 A | 9/1998 | Clauser |
| 2007/0183579 A1 | 8/2007 | Baumann et al. |

(Continued)

FOREIGN PATENT DOCUMENTS

WO 2004/012209 A1 2/2004

OTHER PUBLICATIONS

Alexander Sasov, et. al., "New Type of X-Ray Source for Lensless Laboratory Nano-CT with 50nm Resolution", Proceedings of SPIE, 2010, pp. 78040Q-1 thru 78040Q-8, SPIE, Bellingham, WA, USA, XP040543563.

*Primary Examiner* — Hoon Song
(74) *Attorney, Agent, or Firm* — Baker & Hostetler LLP (57) ABSTRACT

In the field of resolution test charts for analysis of the resolution of X-ray tomography systems, a test chart comprises a substrate bearing X-ray absorbent zones, with widths and spacings to allow measurement of the system resolution. To avoid shadow effects when the X-ray illumination beam is divergent and when the absorbent zones have a large height/width ratio (from 2 to 5 for example), the absorbent zones in the diverse points of the pattern have a shape of which a general direction of elevation with respect to the surface of the substrate is rotated toward a point of convergence which is the same for all absorbent zones. The X-ray source is placed at the convergence point, eliminating shadow effects. The oblique elevation can be obtained by specific etching steps, or curvature of the substrate after fabrication of the absorbent patterns, or else by use of two superimposed partial test charts.

14 Claims, 4 Drawing Sheets

(56) References Cited

U.S. PATENT DOCUMENTS

| | | | |
|---|---|---|---|
| 2007/0183582 A1* | 8/2007 | Baumann | A61B 6/484 378/145 |
| 2007/0183583 A1 | 8/2007 | Baumann et al. | |
| 2012/0002785 A1* | 1/2012 | Kaneko | G21K 1/067 378/62 |
| 2012/0057677 A1* | 3/2012 | Vogtmeier | G02B 5/1857 378/85 |
| 2012/0140883 A1 | 6/2012 | Iwakiri et al. | |

* cited by examiner

RESOLUTION TEST CHART FOR X-RAY IMAGING SYSTEM AND METHOD OF FABRICATION

CROSS-REFERENCE TO RELATED APPLICATION

This application claims priority to foreign French patent application No. FR 1362587, filed on Dec. 13, 2013, the disclosure of which is incorporated by reference in its entirety.

FIELD OF THE INVENTION

The invention relates to resolution test charts for the analysis of the resolution of X-ray tomography systems. A resolution test chart is a plate bearing tightly spaced patterns of X-ray absorbent material; this plate is exposed to X-rays in an imaging system and produces a digital or photographic image of the patterns of absorbent material. The contrast of the image is observed on the various patterns so as to culminate in a value of resolution of the imaging system. The knowledge of this resolution is an important item of data in respect of the subsequent use of the system.

BACKGROUND

X-ray imaging systems may be intended for the observation of structures of very small dimensions, of the order of a few tens of nanometers wide, that may be buried at a depth of several tens of micrometers in a structure to be analyzed. Currently, X-ray tomography systems with resolutions of down to as little as 50 nanometers are available. To measure this resolution, it is therefore necessary to use resolution test charts with extremely small patterns, having widths and spacings of down to as little as a few tens of nanometers.

The resolution test charts envisaged here consist of networks of parallel (straight or curved) or radial lines of an X-ray absorbent material, such as gold, platinum, hafnium, or materials which are slightly less absorbent but easier to etch such as tungsten or tantalum or compositions based on these materials, such as tantalum nitride. The absorbent material is deposited on a substrate transparent to X-rays, for example on a thin silicon membrane, or else buried in the thickness of this substrate. For test charts of high resolution, the pattern is produced by a technique of electron beam lithography followed by plasma etching. The spacing of the lines and their width vary according to the position of the patterns in the test chart and the spacings and widths are known for each position. The resolution is read off directly by observing on the photographic or digital image of the test chart, illuminated by X-rays, the positions in which the contrast between absorbent lines is sufficient and the positions in which it becomes insufficient to properly distinguish two neighboring lines.

Given that X-rays are very penetrating, the patterns of the test chart must be sufficiently absorbent, that is to say they must not only consist of an intrinsically absorbent material but also have a sizable thickness. Moreover, the material used must be relatively easy to etch, including over a sizable height, and it is therefore not always possible to choose materials which are intrinsically the most absorbent (gold or platinum for example). For materials that are easier to etch, such as tungsten, but less absorbent, there may be a need to produce patterns whose thickness is several times larger than the width or the spacing of the patterns.

When the illumination of the test chart is carried out by a parallel X-ray beam, the measurement works well. Such is the case when the X-rays are obtained by synchrotron radiation. But in the general case, X-ray sources provide a divergent beam. If the thickness of the material is not small with respect to the width of the patterns, it results in a phenomenon of non-uniform absorption and of shadowing in respect of the X-rays which have an oblique incidence: on the one hand the absorption is not uniform throughout the width of an absorbent zone and on the other hand absorption is noted between two absorbent zones where there should not be any. The contrast thereof is greatly decreased and impairs the resolution measurement.

This is illustrated in FIG. 1 which is a transverse cut through the test chart, in a plane which contains the axis of the beam X and which is perpendicular to several parallel lines of absorbent zones. The absorbent material, of height H, is deposited on the surface of a membrane MB; it could also be buried in this membrane. The cut of an absorbent line is portrayed by a black mark. Here the lines have a constant width L and a constant spacing E which may be equal to L. The height H is greater than the width L and than the spacing E. The height or depth H of the absorbent material is measured perpendicularly to the plane surface of the membrane. The width L and the spacing E of the lines are measured perpendicularly to the parallel lines.

For X-rays incident perpendicularly to the test chart, that is to say parallel to the direction of the height of the absorbent patterns, there is no problem of shadowing (FIG. 1A); such is the case when the X-rays are provided by a non-divergent source such as a synchrotron. The spatial absorption pattern Ab which results from this non-divergent illumination is drawn alongside the pattern of absorbent zones. This absorption pattern, gathered on a photographic plate or on a digital radiological image sensor, is binary and exactly reproduces the pattern of absorbent zones; it comprises spans of constant maximum absorption where an absorbent zone is present, alternating with spans of minimum absorption, where there is none.

But for divergent X-rays provided by a conventional commercial source X (FIG. 1B), the absorption pattern Ab becomes different and all the more different the more the obliquity of the rays increases. Thus, toward the center of the test chart, the absorption pattern remains practically binary with spans of maximum absorption of width L and of spacing E. But the further one gets from the center, the more the absorption curve deforms and ceases to be binary: absorption is present over a width L' greater than L, increasing from a minimum value up to a maximum value and returns to the minimum value, and remains at its minimum value over a width E' of less than E. Each absorption span therefore comprises a span of maximum absorption and a progressively decreasing absorption. The contrast thereof is impaired in proportion to the obliquity of the incident rays.

Figure 1A:
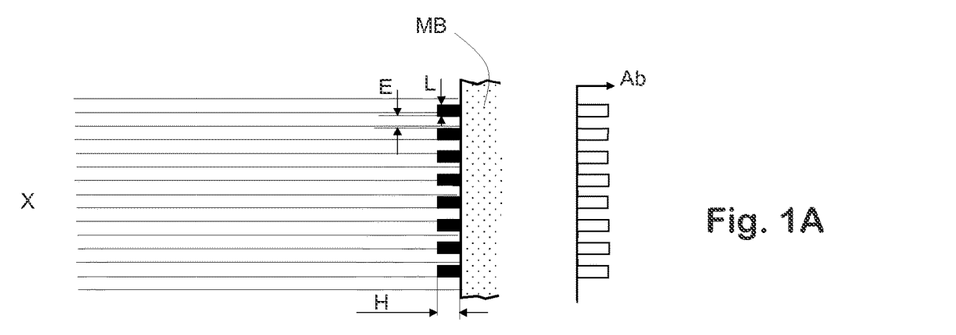
FIGS. 1A-1C already described represents a resolution test chart illuminated by a non-divergent X-ray source (FIG. 1A) and by a divergent X-ray source (FIGS. 1B and 1C)
Figure 1B:
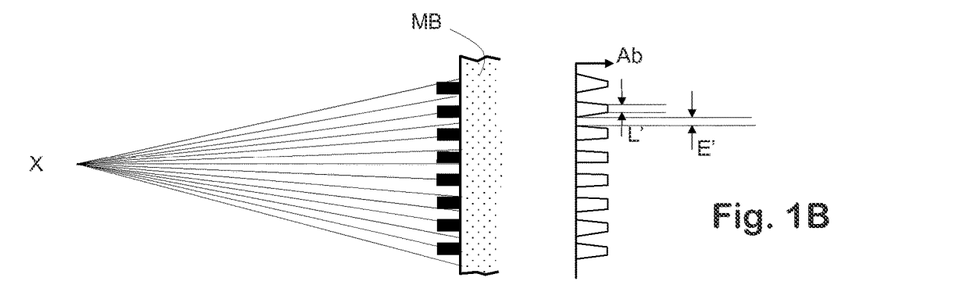
Figure 1C:
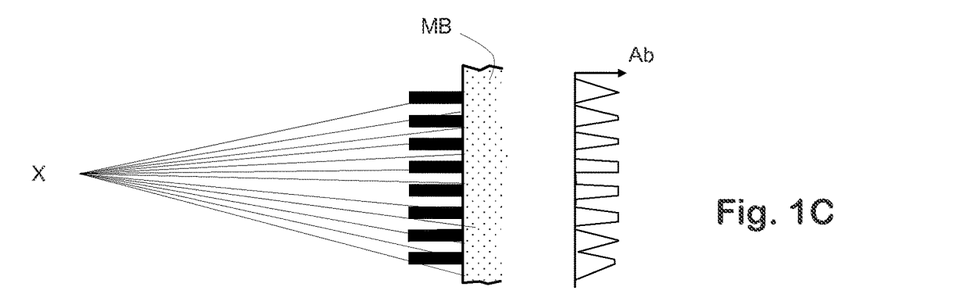

The loss of contrast is all the larger the larger the height H and the larger the angle of obliquity. FIG. 1C represents this shadow effect for a larger height H than in FIG. 1B. In FIGS. 1B and 1C, the angles of obliquity are exaggerated to facilitate reading.

As the height H is dictated by the necessity to have sufficient absorption of the X-rays, there is a snag when it is desired to measure a resolution using patterns of smaller or much smaller width and spacing than this height, that is to say absorbent patterns with an aspect ratio H/L or H/E equal to 2 to 5, or indeed more.

Typically, with tungsten, there may be a need for absorbent patterns 100 nanometers in height and 25 nanometers in width. Moreover, it is not always possible to be content to have patterns of high resolution at the center of the test chart; there may be need to measure the resolution on the edges too.

This may result in the conclusion that the resolution of the imaging system is insufficient, not because it really is but because the procedure for measuring the resolution is affected by an error due to the construction of the test chart.

SUMMARY OF THE INVENTION

The present invention is a resolution test chart for X-ray imaging system, comprising a substrate bearing X-ray absorbent zones, whose widths and spacings are chosen so as to allow a measurement of the resolution of the system, characterized in that the absorbent zones in the diverse points of the pattern have a shape of which a general direction of elevation with respect to the surface of the substrate is rotated toward a point of convergence (at finite distance) which is the same for all the absorbent zones.

Consequently, instead of the absorbent zones all being oriented in elevation parallel to one and the same axis, they are oriented along convergent oblique directions of elevation. The point of convergence is that where the X-ray source will be placed in the use of the test chart.

The absorbent zones may be zones each having a generally conical shape (cone or portion of cone) whose vertex is the point of convergence. These absorbent zones preferably have an aspect ratio of greater than two (preferably from two to five), that is to say the height (in the direction of the point of convergence, along a generator of the cone) is at least two times greater and preferably from two to five times greater than the width of the zone. If the patterns are parallel lines, the width of the zone is the width measured perpendicularly to these lines. The test chart can comprise a pattern of concentric circular parallel lines (circles or portions of circles), that is to say it comprises a series of several conical absorbent zones of different vertex angles, having cone directors which are portions of concentric circular lines. These concentric lines are preferably spaced radially apart by one and the same spacing value which is preferably equal to the width of the zones. There are preferably several series of conical zones such as these, and the values of spacings and widths may be different from one group to the other.

For technological reasons of test chart fabrication, the conical shapes mentioned hereinabove are usually approximate shapes, provided that they reduce the shadow effect mentioned hereinabove just where the obliquity of the X-rays would produce such an effect on a completely vertical elevation zone. To give this approximately conical shape reducing the shadow effects, provision is preferably made for each zone to be constructed on the basis of the juxtaposition of sub-zones of different heights, forming on a lateral edge of the zone a sort of staircase producing an oblique elevation overall slope.

In a different embodiment, provision is made for the membrane which supports the absorbent zones to be curved as a portion of a sphere, with a center of curvature situated at the desired point of convergence. In this case, there is advantage in forming the test chart according to a conventional method (absorbent zones all elevated perpendicularly to the surface of a membrane (or buried perpendicularly to this surface), and in thereafter curving the membrane by peripheral stress or by applying a differential pressure between the opposite faces of the membrane. In this embodiment, the parallel lines of absorbent zones may be concentric circular lines or straight lines.

In another embodiment, compatible with the previous embodiments, the test chart can consist of at least two partial test charts disposed one behind the other in a main direction of illumination; each test chart comprises absorbent zones, the patterns of absorbent zones of the two test charts being similar and disposed according to a homothety in such a way that two absorbent zones which correspond in the two test charts are aligned along a characteristic direction, all the characteristic directions of alignment converging toward the point of convergence. In this embodiment, it is the sum of the heights of the absorbent zones which produces the absorption, and consequently the height of the zones of each test chart can be less than that which is necessary when there is only a single test chart. It is then considered that the general direction of elevation of the absorbent zones with respect to the surface of the substrate is the direction which joins two absorbent zones which correspond in the patterns of the two partial test charts and not the direction of elevation of each of these two zones with respect to the surface which bears it; indeed, since the height of each zone is small, its own direction of elevation is of little importance and may be perpendicular to the substrate even if it is plane.

In this embodiment also, the lines of absorbent zones can be straight or circular.

For the fabrication of the test chart according to the invention, it is possible to envisage several procedures, depending notably on the fact that the test chart is or is not made with the aid of two or more partial test charts.

If it is made with a single test chart and if the substrate of the test chart is plane, the absorbent zones are formed by deposition of a resin and by electron beam lithography and then etching of the absorbent material with a division of each absorbent pattern into juxtaposed sub-zones of smaller widths than the width of the zone, and of different heights, giving an oblique slope at a lateral edge of the zone.

If the test chart is made of at least two partial test charts superimposed at a distance d from one another, it will be possible to lithograph each of the two test charts by an electron beam lithographic method, by calculating the pattern of the second partial test chart so that it reproduces the pattern of the first partial test chart with a homothety of ratio $(D+d)/D$, where D is the distance between the first test chart and the point of convergence where it is desired to place the X-ray source.

In another method, it is possible to lithograph the first partial test chart by a lithography method (electron beam or other), and to make use of the first partial test chart as lithography mask of a second partial test chart in an X-ray lithography method; the X-ray source will be placed at a distance D from the first test chart and the second test chart will be placed behind the first and at a distance d from the first; the pattern etched in the second test chart will be homothetic to the pattern etched in the first test chart, with a homothety ratio $(D+d)/D$.

BRIEF DESCRIPTION OF THE DRAWINGS

Other characteristics and advantages of the invention will become apparent on reading the detailed description which follows and which is given with reference to the appended drawings in which.

DETAILED DESCRIPTION

Figure 2:
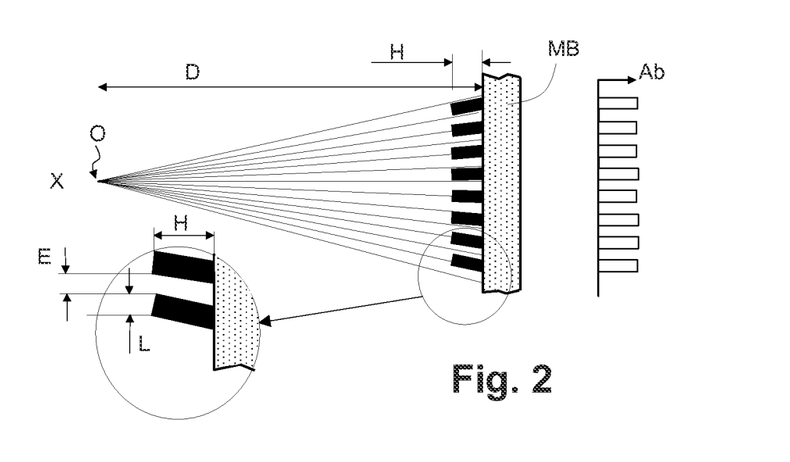
FIG. 2 represents a resolution test chart according to the invention, viewed in section in a plane containing the axis of the X-ray beam and perpendicular to the parallel lines of the pattern.

FIG. 2 represents a vertical sectional cut through a test chart according to the invention, illuminated by a divergent X-ray beam from a point O. The angle of divergence has been represented wider than it is in reality, so as to better depict the particular features of the invention. A typical order of magnitude of angle of divergence is from 3 to 5°. For an X-ray source consisting of an anode bombarded by a high energy electron beam, the point O is the anode point which receives the electron beam. Usually, the anode is enclosed in a casing having an aperture which limits the solid angle of emission of the X-rays. The aperture angle represented is larger than in reality.

The test chart can be formed by absorbent patterns deposited on the plane surface of a substrate or buried in this substrate. The substrate is preferably a fine membrane MB transparent to X-rays, preferably a silicon membrane some hundred nanometers thick. The absorbent patterns are each shaped in the form of a portion of cone, and, for a determined absorbent zone, the vertex angle of the cone corresponds to the angle of illumination by the X-ray source; stated otherwise, if the test chart is formed in a plane membrane 10, each absorbent zone represented in FIG. 2 by a black surface is inclined with respect to the plane of the membrane by an angle which is all the more sizable the further the zone is from the center of the test chart, that is to say from the part of the test chart which is struck by the central axis of the X-ray beam during the use of the test chart. The inclinations all converge toward the X-ray source or in other words toward one and the same common point of convergence O where the X-ray source must be placed for the best possible operation of the test chart, the plane of the test chart being perpendicular to the central axis of the X-ray beam.

The direction of maximum absorption by the absorbent zone is therefore always oriented toward the same point of convergence whatever the position of the absorption zone in the test chart. It follows from this that the contrast is practically the same as in the case of FIG. 1A where the X radiation is non-divergent and the absorbent zones are erected perpendicularly to the substrate (FIG. 1A). The variation in absorption Ab is represented alongside the test chart in FIG. 2; it has a binary appearance throughout the surface illuminated by the X-ray source placed at the point O. In contradistinction to what was seen in FIG. 1B, there is no partial absorption on the edges of the absorbent zones by rays which would be oblique with respect to the general inclination of the absorbent zone. For a pattern of zones having a constant width L and a constant spacing E, the curve of absorption variation exhibits sharp spans of width L and of spacing E with no reduction of contrast.

Figure 3:
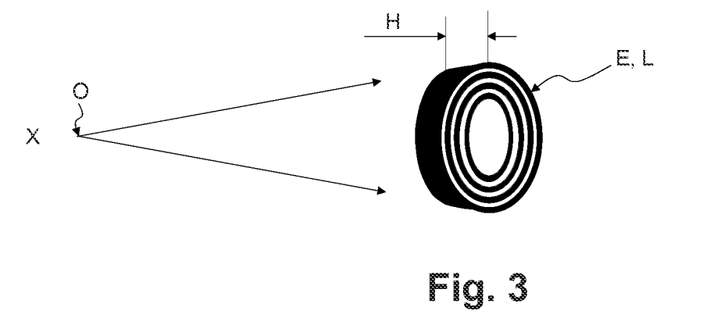
FIG. 3 represents a perspective view of the test chart of FIG. 2 (without the substrate which bears the absorbent patterns)

FIG. 3 represents a perspective view corresponding to the test chart of FIG. 2, showing more clearly what is meant by cone shape or portion of cone shape of an absorbent pattern. The membrane MB is not represented, only the absorbent zones are represented. Viewed end-on looking at the test chart toward the point O, or viewed in section perpendicular to the central axis of symmetry of the illumination, the absorbent zones are concentric annuli of constant width L and of constant spacing E. Viewed in section in a plane containing the axis of symmetry of the illumination (FIG. 2), they are approximately rectangles of width L and of length H. But in three-dimensional space (FIG. 3), these zones each consist of a portion, of height H, of conical surface with circular base and having a certain thickness L; each absorbent zone with circular base corresponds to a cone of different vertex angle, all the cones having the same vertex O.

In an exemplary embodiment, the test chart is constructed with the following geometric parameters:
total angle of conicity: 7° (−3.5° to +3.5°)
height H of the absorbent patterns: 200 nm
distribution interval (E+L) of the concentric circular lines of the base of the cones: 50 nm.

The test chart can comprise several series of concentric lines with a different spacing interval in the various series, the most tightly spaced patterns being at the center and the wider patterns at the periphery.

Figure 4:
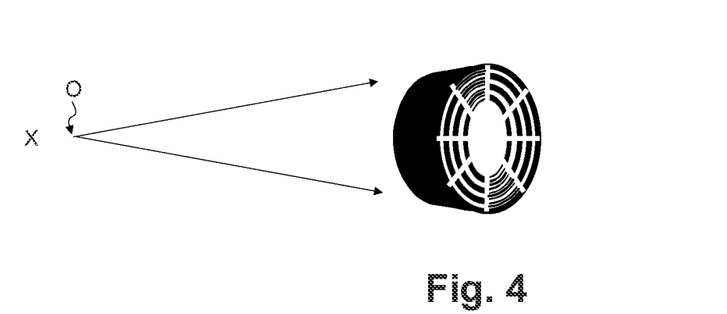
FIG. 4 represents a perspective view of another exemplary test chart with angular sectors in which absorbent zones in portions of cones are formed, with widths and spacings of patterns which differ from one zone to the other.

Represented in FIG. 4 is a variant embodiment in which the absorbent zones are portions of cone whose bases are portions of concentric circles and not complete circles as in FIG. 3. The widths and spacings of the concentric annuli may be different from one circular arc portion to another, as is represented.

But the resolution measurement can also be carried out using several different test charts such as that of FIG. 2, test charts for which the distribution intervals of the concentric lines are different from one another.

During the use of the test chart, it is understood that it must be centered with respect to the X-ray beam, and disposed perpendicularly to the central axis of the beam; it must be placed at a distance D such that the point of emission of the X-ray beam is situated at the vertex O of the cones which all converge to this point. The test chart is placed at the known distance D, or else its desired location is determined by experimentation; in the second case, the test chart will be placed at diverse positions and orientations until the position and orientation which provides the best contrast over the whole of the test chart is found.

In the foregoing, it has been considered that the patterns of absorbent zones are defined by concentric circular lines;

if it is considered that an absorbent zone defined by a circular line or a circular line portion consists of a multitude of elementary zones, it may be said that the general direction of the elevation of the elementary absorbent zones belonging to a given line is oriented obliquely, always with the same value of angle with respect to the support surface of the test chart on which the zones are erected, whatever the position of the elementary zone along the circular line. It would optionally be possible to envisage that the patterns of absorbent zones are not concentric patterns but are parallel straight lines or lines disposed radially in a fan; however these solutions are not preferred since the oblique direction to be given to the elevation of the elementary absorbent zones of a line would no longer be constant along one and the same line, and this may significantly complicate the embodiment.

We shall return further on to the way to produce absorbent zones in the form of cones or portions of cones, it being understood that this entails approximations of cones having regard to the technological constraints.

Figure 5:
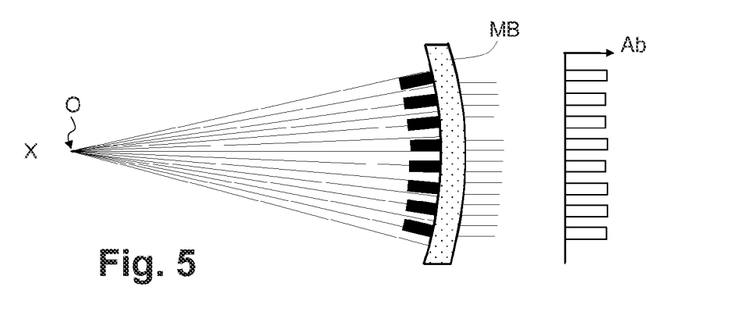
FIG. 5 represents a sectional view of a variant embodiment of the invention.

In another embodiment, represented in FIG. 5, provision is made for the surface of the membrane MB to be a portion of sphere whose center of curvature is the point O where it is desired to place the X-ray source. The absorbent zones are then patterns elevated perpendicularly to the surface at every point, and their direction of elevation is therefore different depending on the site where the absorbent zone is situated. All the directions of elevation converge to one and the same point of convergence O which is the center of curvature of the portion of sphere. To produce such a test chart, absorbent zones will be etched according to conventional methods on a plane membrane, the absorbent zones then all having an elevation perpendicular to the plane of the membrane, and thereafter the membrane will be curved, either by exerting stress uniformly right around its periphery, or by applying a differential pressure between the opposite faces of the membrane. This is possible for thin membranes, for example silicon membranes. The absorbent zones then have elevations which remain perpendicular at all points to the membrane and which therefore converge toward the latter's center of curvature.

Figure 6:
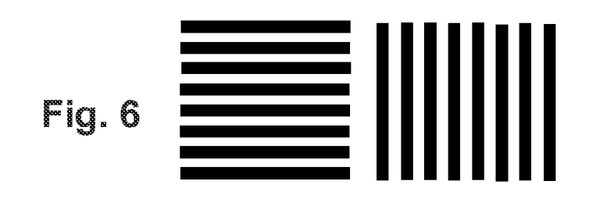
FIG. 6 represents an end-on view of a test chart of horizontal and vertical parallel absorbent lines.

With a test chart constructed in this way, it is very possible to use parallel straight lines such as those of FIG. 6, rather than concentric circular lines as in FIG. 3, as test chart pattern. The general direction of elevation at an arbitrary point of the line will not be constant for all the points of the line, but it will be inclined naturally with respect to the axis of the X-ray beam all the more the further this point is from the center of the test chart (center defined by the point of impact of a central ray of the X-ray beam when the test chart is properly placed).

Figure 7:
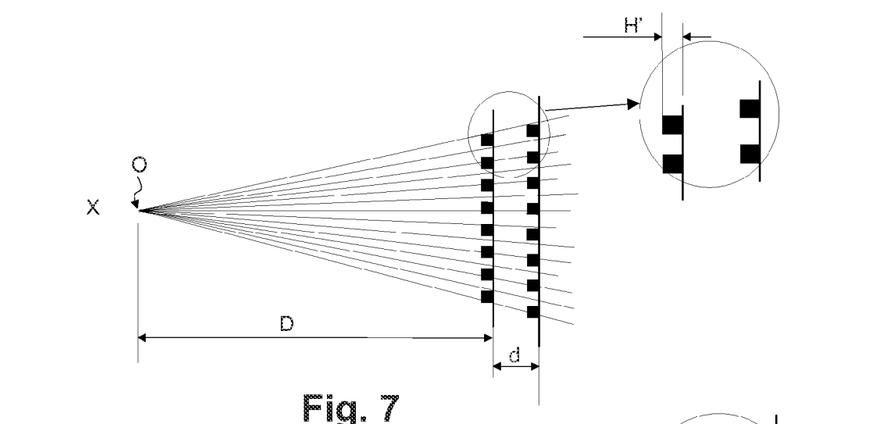
FIG. 7 represents a sectional view of a test chart formed of two partial test charts with homothetically located patterns.

FIG. 7 represents another construction of resolution test chart according to the invention, aimed at facilitating production while avoiding having too large an aspect ratio H/L for the absorbent zones. Instead of having a test chart comprising absorbent zones of sufficient height H to strongly absorb the X-rays, the test chart is now constructed of two parallel partial test charts (or more) a distance d apart, each comprising absorbent zones of height H' smaller than H. The sum of the heights H' (identical or not in the various test charts) corresponds to the desired height in order to have sufficient absorption. The patterns of absorbent zones are similar in the two test charts: an elementary absorbent zone of each partial test chart is correspondingly matched with a respective elementary zone of the other test chart or of the other test charts. This correspondence is achieved with a positioning homothety, defined with respect to the vertex O of the illumination cone, that is to say with respect to the site where it is desired to place an X-ray source. This means that the position of an elementary absorbent zone of a partial test chart and the position of the corresponding elementary absorbent zone of the other test chart are situated on a straight line and that all the straight lines which thus join elementary absorbent zones which correspond convergent at one and the same point.

This structure with two or more partial test charts makes it possible to limit the height of the individual absorbent zones, while summing their absorptions. In this case, it is not necessary to worry about the direction of elevation of each zone with respect to the surface of the membrane since the height H' can be low enough not to cause shadow phenomena; the direction of elevation that has to be considered now and which must be oblique is then the direction joining two elementary zones which correspond in the two partial test charts.

Figure 8:
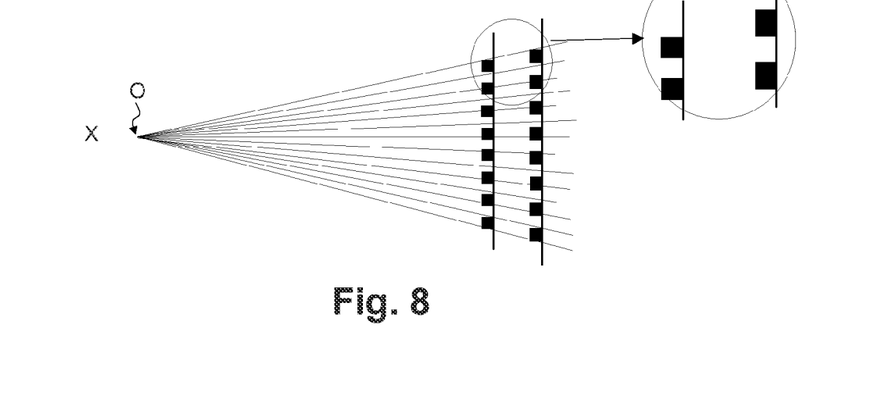
FIG. 8 represents a sectional view of another exemplary test chart formed of two partial test charts with homothetic patterns.

In FIG. 7, this positioning homothety has been represented with absorbent zones of the same width in the two test charts. In FIG. 8, it is considered moreover that there is a homothety of dimensions of the widths and spacings of the absorbent zones, thereby further improving the contrast.

The configurations of FIGS. 7 and 8 make it possible to use patterns of absorbent zones which are not concentric as in FIGS. 3 and 4 and which may notably be patterns of parallel lines, such as those represented in FIG. 6. The patterns of one of the partial test charts are in fact deduced by calculation of the patterns of the first line whatever the shape of the pattern without having to calculate a general direction of elevation of a point of an absorbent zone as a function of the position of this point with respect to the center of the test chart.

It is even possible to produce the pattern of a second test chart directly from the pattern of a first test chart without calculation if the test charts are produced by a method which itself involves in a natural manner an intrinsic homothety of patterns.

Figures 9, 10:
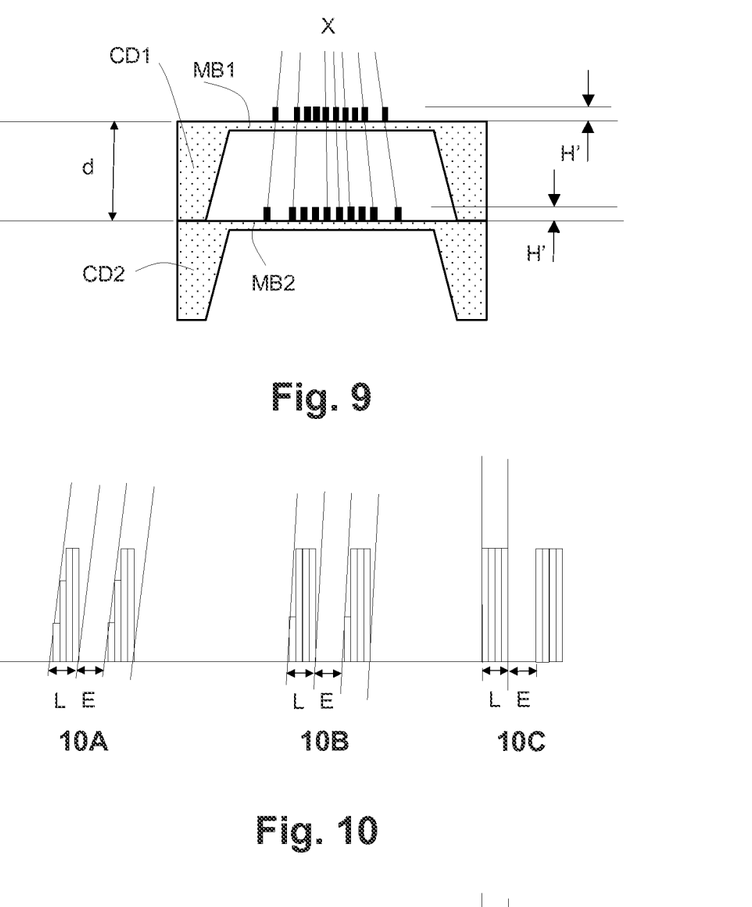
FIG. 9 represents a test chart formed of two superimposed partial test charts with homothetic patterns, the second test chart being produced by exposure to X-rays through the first test chart, with a divergent X-ray source.
FIG. 10 represents a step of a method for forming absorbent zones of shape approximating a conical shape by juxtaposition of narrow resin bands of different heights.

FIG. 9 represents a resolution test chart formed of the superposition of two partial test charts. It would be possible to have three or more superimposed partial test charts. The absorbent zones of the partial test charts are formed for example on respective silicon membranes MB1 and MB2 tensioned on silicon frames CD1 and CD2. The spacing d between the two test charts is equal to the thickness of the silicon frames, for example a standard thickness of 750 micrometers. The thickness of the membrane may be 100 or 200 nanometers. The height H' of the patterns may be of the order of 50 nanometers. The test charts can have a surface area of 1 $mm^2$. The drawings are not to scale to facilitate understanding.

To produce this test chart, it is possible to fabricate each test chart by an electron beam lithography method, particularly adapted for line widths and/or spacings down to as little as 20 nanometers or indeed even 10 nanometers, after having calculated by homothety the shapes and positions of the absorbent patterns of the second test chart on the basis of the shapes and positions of the patterns of the first test chart. The first test chart is the lower test chart and it is produced in a first operation of electron beam lithography followed by etching of the absorbent material; the second test chart is then put in place above the first and it is lithographed with its own pattern, homothetic to the first with a homothety ratio $D/(D+d)$ where d is the distance between test charts and D the distance of the second test chart from the desired point of convergence O; the second test chart is lithographed like the first by electron beam lithography, while complying with an alignment of the two patterns, this being easily achievable with marks etched on the first test chart, given that the membrane is transparent and allows the pattern of the first test chart to be seen.

The electron beam lithography of the partial test charts can be done by conventional methods of transfer of etched patterns into a resin sensitive to the electron beam. The resin pattern transfer can be done directly or by way of an intermediate etching of a hard mask. The method can be as follows:

deposition of an absorbent material, for example tungsten, of height H' or greater than H', on the surface of a fine silicon membrane held tensioned by a peripheral frame, deposition of a resin sensitive to the electron beam on the absorbent material;

writing of the pattern into the resin by an electron beam and chemical development of the resin;

transfer of the resin pattern remaining into the absorbent layer, by vertical anisotropic etching of the absorbent layer with a product which more quickly attacks the absorbent material than the developed resin.

A transfer by way of a hard mask layer (made of carbon for example) can also be envisaged: in this case a hard mask layer is deposited on the absorbent layer before deposition of the resin, and the developed resin pattern serves to etch the hard mask and not the absorbent layer, with an etching product which attacks the hard mask more quickly than the developed resin; then, it is this hard mask which serves to protect the absorbent layer where it must not be removed; the absorbent material is then attacked with an etching product which attacks the absorbent material more quickly than the hard mask.

Instead of etching the two test charts successively with an electron beam, it is also possible to use a first upper test chart lithographed by electron beam, and then put in place a second test chart below the first, and to lithograph the second test chart by a method of X-ray lithography having the same divergence as the beam of the apparatus for which the test chart is intended. Indeed, the first test chart can serve as lithography mask since it is formed of a pattern of X-ray absorbent material. The second test chart will therefore be coated not with a resin sensitive to an electron beam but with a resin sensitive to X-rays. The homothety in the ratio (D+d)/D of the second test chart with respect to the first test chart will be obtained entirely naturally provided that the X-ray source is placed at the distance D from the first test chart. Here again, the etching can be done directly with transfer of the resin pattern into the absorbent layer of the lower test chart or indirectly by transfer of the resin pattern into a hard mask layer and then transfer of the pattern of the hard mask layer into the absorbent layer.

To obtain a test chart such as that of FIG. 5, electron beam lithography on a plane membrane is undertaken as explained hereinabove in regard to the partial test charts, and the membrane is subsequently curved so as to give it a spherical shape, by differential pressure between the two faces, or by peripheral stress.

To obtain patterns whose surface is approximately conical in the case of the test charts such as those of FIGS. 2, 3, 4, on the basis of absorbent zones formed on a plane membrane surface which is not intended to be curved subsequently, it is possible to lithograph absorbent zones in the form of ladders, that is to say zones of non-uniform height over the whole of the width L of the zone.

Again one undertakes electron beam lithography using a resin sensitive to electrons and a transfer of the resin pattern into the absorbent layer, by exposing the resin over very narrow bands and over non-uniform heights: resin zones of aggregate width L are formed by juxtaposing several zones of smaller width $L_m=L/m$, these zones having different heights related to the desired obliquity with respect to the plane of the membrane. Zones of width of the order of 10 nanometers, or indeed less with strongly accelerated electron beams, for example above 50 kilovolts, can be written into the resin by the electron beams. The height of the resin in a narrow band corresponding to the width of the electron beam is adjusted by the duration of exposure to the beam. If the desired resolution is a width L of the order of 50 nanometers, it is possible to form resin zones of width L by juxtaposing 3 to 5 patterns of width $L_m$ equal to 10 to 20 nanometers.

FIG. 10 explains this principle by showing three different resin patterns corresponding to three different desired obliquities, of the order of a few degrees. In FIG. 10A, the approximately conical surface shape is obtained with a development of the resin zones over four juxtaposed bands two of which have a maximum height and the other two have stair-like tiered heights. The height of the stairs is chosen so as to eliminate as far as possible the shadow which would exist if the height of the resin were uniform over the four bands. In FIG. 10B, where the desired obliquity is less, a single band is exposed with a lower height than the others, and, here again, the absence of shadow resulting therefrom is adapted to the obliquity of the X-rays which will strike this zone during the use of the test chart. Finally, FIG. 10C represents a resin pattern of elevation perpendicular to the surface, for a central absorbent zone of the test chart; such a pattern does not require tiered heights of the various bands of width L/M.

In these configurations, the conicity of the shape of the absorbent zones is the conicity of the outer lateral edge of the zones, that is to say the edge furthest from the center of the test chart, since it is this outer edge and not the inner edge which produces an undesirable shadow of the space between two zones. What is then meant by "general direction of elevation" of an absorbent zone with respect to the surface of the substrate is then the oblique direction of this outer edge of the zone.

The tiered resin pattern in juxtaposed narrow bands is transferred into the absorbent layer by anisotropic plasma etching to establish a pattern of absorbent zones of tiered heights in correspondence with the resin pattern of tiered heights. The tiering of heights can indeed be preserved in the transfer process, whether this be direct transfer of the resin pattern into the absorbent layer or indirect transfer by way of a hard mask layer.

Figure 11:
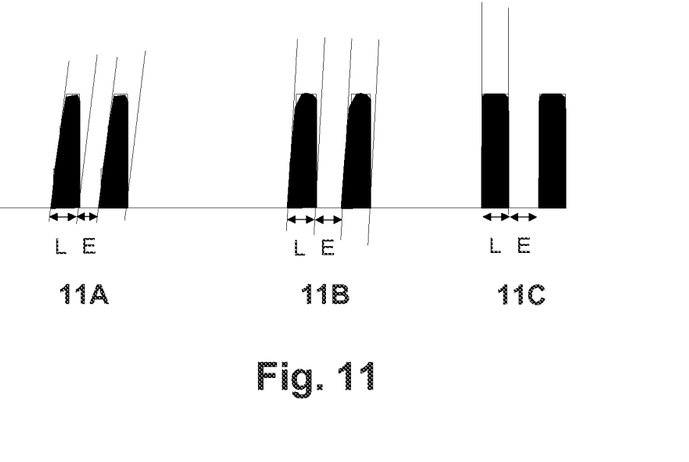
FIG. 11 represents the absorbent zones formed by the transfer, by etching of the absorbent material, of the result of the step of FIG. 10.

In the practical embodiment, since the etchings are not perfectly anisotropic, a smoothing of the tiered shape will occur naturally during direct or indirect transfers of the resin pattern, culminating in the conical surface shapes of the absorbent zones represented in FIG. 11 and in which it is seen that there is no or almost no shadow detrimental to contrast.

The preferred absorbent materials according to the invention are tungsten, tantalum, tantalum nitride. According to the mode of etching used, other materials may be used: gold and platinum can be etched by ion etching, and in this case the zones can be etched directly while giving them an obliquity controlled by the inclination of the ion bombardment beam, but the height/width ratio of the zone is then smaller (of the order of 1) than in the case of tungsten etched by plasma anisotropic etching; this is why, in the case of gold and platinum, it is preferable to adopt a configuration with two or more partial test charts, such as that of FIGS. 7 and 8 even if the absorbent zones of each test chart also have an individual obliquity (not represented) over their reduced height H'.

It is also possible to envisage combining ion etching and plasma etching, so as to benefit in part from the advantage of adjustable oblique ion etching.

The invention claimed is:

1. A method for measuring the spatial resolution of an X-ray imaging system comprising the following steps:
    providing a resolution test chart comprising a substrate bearing X-ray absorbent zones, whose widths and spacings are configured to allow a measurement of the resolution of the system, wherein the absorbent zones in the diverse points of a pattern have a shape of which a general direction of elevation with respect to the surface of the substrate is rotated toward a point of convergence which is the same for all the absorbent zones;
    directing an X-ray beam, diverging from signal point of convergence of the absorbent zones, towards the resolution test chart;
    using the X-ray imaging system for acquiring an image of the resolution test chart illuminated by the X-ray beam, said image comprising a pattern of lines corresponding to the absorbent zones of the resolution test chart; and
    measuring the contrast of said pattern of lines and deducing therefrom the spatial resolution of the X-ray imaging system.

2. The method for measuring the spatial resolution of an X-ray imaging system as claimed in claim 1, wherein said absorbent zones each have a surface shaped in the form of a portion of cone, whose vertex is the point of convergence.

3. The method for measuring the spatial resolution of an X-ray imaging system as claimed in claim 1, wherein a height of the zone in the direction of the elevation with respect to the surface of the substrate is at least two times greater and preferably from two to five times greater than the width of the zone.

4. The method for measuring the spatial resolution of an X-ray imaging system as claimed in claim 1, wherein said resolution test chart comprises a series of several conical absorbent zones of different vertex angles.

5. The method for measuring the spatial resolution of an X-ray imaging system as claimed in claim 4, wherein said conical shaped absorbent zones of said test chart are spaced apart by one and the same angular spacing value.

6. The method for measuring the spatial resolution of an X-ray imaging system as claimed in claim 5, wherein said resolution test chart comprises several series of conical absorbent zones whose vertex angles differ from one another and which are spaced radially apart by a different angular value of spacing for the various series.

7. The method for measuring the spatial resolution of an X-ray imaging system as claimed in claim 1, wherein the surface of said resolution test chart is shaped as a portion of a sphere and the absorbent zones have at any point a direction of elevation perpendicular to the surface.

8. The method for measuring the spatial resolution of an X-ray imaging system as claimed in claim 1, wherein said resolution test chart comprises at least two partial test charts placed one behind the other, each comprising absorbent zones, the patterns of absorbent zones of the two test charts being similar and disposed according to a homothety in such a way that the positions of two absorbent zones which correspond in the two test charts are aligned along a characteristic direction, all the characteristic directions of alignment converging toward the point of convergence.

9. The method for measuring the spatial resolution of an X-ray imaging system as claimed in claim 8, wherein said patterns of absorbent zones are straight or circular parallel lines of constant spacing.

10. The method for fabricating a spatial resolution test chart as claimed in claim 1, wherein a minimum spacing between two of said absorbent zones is less than a micrometer, the method further comprising the following steps:
    deposition of an X-ray absorbent layer on a plane surface;
    deposition of a resin sensitive to an electron beam;
    writing by an electron beam of narrow resin bands having several different resin heights, juxtaposed to form the width of an absorbent zone; development of the resin; and
    anisotropic plasma etching of the absorbent layer protected by the resin so as to transfer in the absorbent layer a pattern of tiered heights in correspondence with that of the resin.

11. The method for fabricating a spatial resolution test chart as claimed in claim 8, wherein a minimum spacing between said two absorbent zones is less than a micrometer.

12. The method for fabricating a spatial resolution test chart as claimed in claim 11, comprising at least the following steps:
    production of a first partial test chart by electron beam lithography according to a pattern of X-ray absorbent zones;
    placement of the first partial test chart above a substrate of second partial test chart, at a distance d from the first test chart, the substrate of the second test chart being clad with an absorbent layer and with a resin sensitive to X-rays; and
    exposure of the resin of the second test chart, through the first test chart, to a divergent X-ray source placed at a point O a distance D from the first test chart, so as to produce in the second test chart a homothetic pattern of the pattern of the first test chart in a ratio (D+d)/D.

13. The method for fabricating a spatial resolution test chart as claimed in claim 1, wherein a minimum spacing between two of said absorbent zones is less than a hundred nanometers, the method further comprising the following steps:
    deposition of an X-ray absorbent layer on a plane surface;
    deposition of a resin sensitive to an electron beam;
    writing by an electron beam of narrow resin bands having several different resin heights, juxtaposed to form the width of an absorbent zone; development of the resin; and
    anisotropic plasma etching of the absorbent layer protected by the resin so as to transfer in the absorbent layer a pattern of tiered heights in correspondence with that of the resin.

14. The method for fabricating a spatial resolution test chart as claimed in claim 8, wherein a minimum spacing between said two absorbent zones is less than a hundred nanometers.

* * * * *